(12) United States Patent
Casagrande et al.

(10) Patent No.: US 7,687,429 B2
(45) Date of Patent: Mar. 30, 2010

(54) CATALYSTS FOR OXYCHLORINATION OF ETHYLENE TO 1,2-DICHLORETHANE

(75) Inventors: Francesco Casagrande, Novara (IT); Carlo Orsenigo, Milan (IT)

(73) Assignee: Sud Chemie - Catalysts Italia S.R.L., Novara (IT)

( * ) Notice: Subject to any disclaimer, the term of this patent is extended or adjusted under 35 U.S.C. 154(b) by 297 days.

(21) Appl. No.: 11/286,638

(22) Filed: Nov. 23, 2005

(65) Prior Publication Data

US 2006/0129008 A1    Jun. 15, 2006

(30) Foreign Application Priority Data

Dec. 2, 2004    (IT) .......................... MI2004A2317

(51) Int. Cl.
| | |
|---|---|
| B01J 27/122 | (2006.01) |
| B01J 27/138 | (2006.01) |
| B01J 27/125 | (2006.01) |
| B01J 23/02 | (2006.01) |
| B01J 23/06 | (2006.01) |
| B01J 23/70 | (2006.01) |
| B01J 23/72 | (2006.01) |
| C07C 17/00 | (2006.01) |
| C07C 19/00 | (2006.01) |

(52) U.S. Cl. .................. 502/225; 502/226; 502/231; 502/340; 502/341; 502/345; 502/346; 570/224; 570/234; 570/245

(58) Field of Classification Search ................ 502/225, 502/226, 231, 340, 341, 345, 346; 570/224, 570/234, 245

See application file for complete search history.

(56) References Cited

U.S. PATENT DOCUMENTS

| | | | | | |
|---|---|---|---|---|---|
| 2,386,518 | A | * | 10/1945 | Upham ....................... | 502/320 |
| 3,642,921 | A | * | 2/1972 | McCarthy et al. ........... | 570/243 |
| 4,329,527 | A | * | 5/1982 | Kuhn et al. ................ | 570/245 |
| 4,460,699 | A | * | 7/1984 | Convers et al. ............. | 502/84 |
| 4,587,230 | A | * | 5/1986 | Cavaterra et al. ........... | 502/225 |
| 4,871,707 | A | * | 10/1989 | Cavaterra et al. ........... | 502/225 |
| 4,910,354 | A | * | 3/1990 | Derleth et al. .............. | 570/243 |
| 5,070,062 | A | * | 12/1991 | Canavesi et al. ............ | 502/225 |
| 5,202,511 | A | * | 4/1993 | Salinas et al. ............... | 570/245 |
| 5,260,247 | A | * | 11/1993 | Helmut et al. .............. | 502/225 |
| 6,703,342 | B1 | * | 3/2004 | Lok ........................... | 502/346 |
| 6,777,373 | B1 | * | 8/2004 | Carmello et al. ............ | 502/346 |
| 6,872,684 | B2 | * | 3/2005 | Casagrande et al. ......... | 502/225 |

FOREIGN PATENT DOCUMENTS

| | | | |
|---|---|---|---|
| EP | 0 119 933 | A | 9/1984 |
| EP | 0 176 432 | A | 4/1986 |
| EP | 1 464 395 | A | 10/2004 |
| GB | 1 345 653 | A | 1/1974 |

* cited by examiner

*Primary Examiner*—Patricia L Hailey
(74) *Attorney, Agent, or Firm*—Husch Blackwell Sanders LLP Welsh & Katz

(57) ABSTRACT

Catalysts for oxychlorination of ethylene to 1,2-dichlorethane, comprising compounds of copper and magnesium supported on gamma alumina, wherein the copper, expressed as metal, is present in a quantity from 7 to 12% by weight and the Mg/Cu ratio is from 0.05 to 1, wherein the distribution of copper in the catalyst particle is such that the ratio X/Y between the concentration of the copper atoms on the surface given by the Al/Cu ratio (X) on the surface (20-30 nm layer) and the concentration given by the Al/Cu ratio (Y) referred to the entire particle is greater than 1.3 and can reach 3.

7 Claims, No Drawings

CATALYSTS FOR OXYCHLORINATION OF ETHYLENE TO 1,2-DICHLORETHANE

The present invention relates to catalysts for oxychlorination of ethylene to 1,2-dichlorethane (1,2-DCE), to the method for their preparation, and to their use in processes for the oxychlorination of ethylene to 1,2-DCE.

BACKGROUND OF THE INVENTION

Catalysts for oxychlorination of ethylene to 1,2-dichlorethane comprising a copper compound, generally cupric chloride, and promoters based on salts of alkaline and/or alkaline-earth metals and rare earths are well-known in the literature.

The copper content of these catalysts generally is no more than 6-8% by weight.

Catalysts with a copper content that can reach 12-14% by weight are known from patent GB 1,189,815.

The catalysts are prepared by co-precipitation of a hydrogel of alumina and copper, followed by aging of the precipitate at 10°-40° C. for at least 10 hours, drying, and finally calcining at a temperature between 300 and 600° C. for a time sufficient to convert the alumina hydrogel into gamma alumina.

Differently from catalysts with a high copper content (12% by weight) obtained by impregnating alumina with a solution of a copper salt, which according to the patent cited above yield low conversions of hydrochloric acid and considerable combustion of the ethylene to carbon oxides, catalysts prepared by co-precipitation provide, again according to the patent, a good performance both in terms of conversion and selectivity and in terms of stability of the fluid bed.

However, these catalysts have the drawback that they require high spatial velocities and a consequent considerable recycling of the unconverted ethylene.

Catalysts with a high copper content (12-13% by weight) (probably prepared according to the co-precipitation method) are commercially available which have high activity but have the drawback of a considerable combustion of the ethylene even when working at relatively low temperatures (210° C.).

European patent application EP 1 464 395 describes catalysts for oxychlorination of ethylene which have a copper content of 7-12% by weight and comprise compounds of magnesium, prepared by impregnation of gamma alumina, which do not have the drawbacks of catalysts obtained by co-precipitation but provide a good performance both in terms of selectivity to 1,2-DCE and in terms of productivity.

The distribution of copper in these catalysts is such that the X/Y ratio, where X is the Al/Cu ratio at the surface, determined by XPS (X-ray Photoemission Spectroscopy) and Y is the Al/Cu ratio referred to the entire particle of catalyst, is comprised in the range between 0.8 and 1.3.

The examples of the European application show that as the X/Y ratio rises from 0.91 to 1.8 (comparison example 1), the performance of the catalyst decreases.

It is also found that a commercially available catalyst with high copper content (12.5% by weight), probably prepared with the co-precipitation method, in which the X/Y ratio is 3, does not have satisfactory selectivity.

In the field of catalysts for oxychlorination of ethylene to 1,2-DCE with a high copper content, the need is felt for catalysts that yield a satisfactory performance even when the X/Y ratio is high. This because a sufficiently high x/Y ratio ensures a long life of the catalyst.

SUMMARY OF THE INVENTION

It has now been found unexpectedly that catalysts comprising compounds of copper and magnesium supported on gamma alumina and in which the copper content is comprised from 7 to 12% by weight and the X/Y ratio is higher than 1.3 and can reach 3 yield a satisfactory performance in terms of conversion, selectivity and sufficiently long life of the catalyst. The satisfactory long life is due to the fact that the copper compounds are concentrated mostly within the pores and are therefore less subject to losses.

DETAILED DESCRIPTION OF THE INVENTION

Copper and magnesium compounds that can be used to prepare catalysts are preferably chlorides. The Mg/Cu ratio in the catalyst is comprised from 0.05 to 1.

The catalysts can also comprise, in addition to copper and magnesium compounds, compounds chosen among those of alkali metals, alkaline earth metals, and/or rare earths.

Cesium and potassium chlorides and mixtures thereof are preferred.

The gamma alumina that can be used has a surface area of 90 to 260 $m^2/g$, a pore volume preferably between 0.3 and 0.6 $cm^3/g$ and a particle size distribution in which the particles with a diameter between 40 and 90 microns are at least 50-70% and at least 30% is constituted by particles with a diameter between 40 and 63 microns or between 63 and 90 microns.

The use of this type of alumina allows to work with high spatial velocities of the reagents without problems of defluidization of the catalytic bed, which occurs particularly when, by working with relatively low reaction temperatures (210° C.), it is necessary to use high spatial velocities in order to maintain the productivity of the reactor at satisfactory values.

By using higher reaction temperatures (220-230° C.), it is possible to use alumina with a particle size distribution comprising particles in which 20-40% have a diameter between 90 and 125 microns, 35-55% have a diameter between 63 and 90 microns, and 10-15% have a diameter between 40 and 63 microns.

The catalyst is prepared by impregnating the alumina in two or more stages, in which the volume of the solution of the salt of copper and magnesium is equal to, or preferably lower than, the pore volume of the alumina during first impregnation, is smaller than the volume used in the first impregnation, for example is 60% of the pore volume, during the second impregnation, and is even lower, for example 40% of the pore volume, in the third impregnation.

Triple impregnation is used preferably when the content of the copper compound to be supported is higher than 9-10% by weight (expressed as copper).

The powder of the first impregnation is dried at 100-130° C. for a sufficient time, for example 16 hours in an oven; this is followed by second impregnation and drying in an oven, and so forth for the successive impregnations.

The solution of the salts is prepared by dissolving them in distilled water and facilitating dissolution by means of bland heating; the solution is then sprayed onto the alumina arranged in a rotating jar. It is also possible to use a fluidized bed.

The solutions are preferably rendered acid by means of hydrochloric acid or other strong acids used in quantities from 0.1 to 1 equivalent per g-atom of copper. These solutions are used in particular when the content of the copper compound to be carried is higher than 9-10% by weight as copper.

As already noted, the distribution of the copper on the surface comprised in a layer of 2-3 nm is determined by XPS (reference is made to U.S. Pat. Nos. 4,587,230 and 4,871,707 for further information).

The oxychlorination process is performed on a fluid bed, using reaction temperatures between 190 and 240° C., Cl/C ratios from 0.5 to 0.7, preferably 0.6-0.65, and oxygen/ethylene molar ratios of 0.3 to 0.5, preferably 0.4-0.5, and linear velocities of 18-22 cm/sec with contact times of 5-10 seconds.

The following examples are given to illustrate but not to limit the scope of the invention.

EXAMPLES

Characteristics of Gamma Alumina Used as Carrier

Four different types (A, B, C and D) were used: their characteristics are listed below.

|  |  | A | B | C | D | E |
|---|---|---|---|---|---|---|
| Physical characteristics |  |  |  |  |  |  |
| Surface area | m²/g | 218 | 248 | 211 | 210 | 219 |
| Pore volume | cm³/g | 0.50 | 0.48 | 0.41 | 0.48 | 0.50 |
| Bulk density | g/cm³ | 0.79 | 0.77 | 0.82 | 0.80 | 0.78 |
| Particle size distribution |  |  |  |  |  |  |
| Fraction of particles with φ > 125 microns | % | 4.7 | 0.7 | 1.8 | 0.6 | 1.5 |
| Fraction of particles with φ between 90 and 125 microns | % | 35.1 | 6.4 | 11.2 | 6.6 | 12.9 |
| Fraction of particles with φ between 63 and 90 microns | % | 44.3 | 32.0 | 30.2 | 32.4 | 39.2 |
| Fraction of particles with φ between 40 and 63 microns | % | 13.8 | 41.6 | 39.4 | 42.3 | 39.5 |
| Fraction of particles with φ below 40 microns | % | 1.4 | 19.3 | 17.4 | 18.1 | 6.9 |

Description of Operating Conditions for Tests in Pilot Plant

The catalysts of Examples 1-6 and of comparison examples 1-2 were tested in a glass reactor provided with a system for controlling the feeds of the reagent gases and a cooling system for condensing and recovering the condensable products. The non-condensables were measured by gas chromatography. During the test, the condensed products were collected in two phases, an aqueous one and an organic one. The two phases were separated and weighed: the organic phase was analyzed by gas-liquid chromatography (GLC) in order to determine the purity of the dichlorethane and check the amount of chlorinated organic byproducts.

The dimensions of the reactor were: inside diameter, 20.6 mm; height, 3200 mm.

All the tests were conducted at the pressure of 1.6 ata with a linear velocity of 21-22 cm/s, working at temperatures between 210 and 230° C. and using $O_2$ as oxidizer.

Some tests were conducted with a Cl/C molar ratio of 0.60-0.63 and an $O_2/C_2H_4$ molar ratio of 0.41-0.43 (test conditions: OXY 1). Other tests were conducted with a Cl/C molar ratio of 0.60-0.63 and an $O_2/C_2H_4$ molar ratio of 0.36-0.38 (test conditions: OXY 2).

The reactor of the pilot plant provided a performance which can be extrapolated to an industrial reactor.

The results of the OXY 1 tests are given in Table 3; the results of the OXY 2 tests are given in Table 4.

The Al/Cu, Y and X values reported in the examples have the meaning and were determined according to the indication given in the specification.

Example 1

1000 g of B gamma $Al_2O_3$ were impregnated a first time in a 5-liter rotating jar at ambient temperature with 400 ml of an aqueous solution having a total volume of 700 ml and containing:

$CuCl_2.2H_2O$=301.0 g;
$MgCl_2.6H_2O$=117.3 g;
HCl 37% by weight=22.0 ml;
remainder: demineralized $H_2O$ up to a volume of 700 ml.

The impregnated powder was dried at 100° C. for 16 hours in an oven previously brought to the intended temperature. This was followed by a second impregnation with the remaining volume of solution, equal to 300 ml, and by final drying at 100° C. for 16 hours in an oven previously brought to the intended temperature.

The chemical and physical characteristics of the catalyst are given in Table 1.

Example 2

1000 g of C gamma $Al_2O_3$ were impregnated a first time in a 5-liter rotating jar at ambient temperature with 400 ml of an aqueous solution having a total volume of 700 ml and containing:

$CuCl_2.2H_2O$=301.0 g;
$MgCl_2$ $6H_2O$=117.3 g;
HCl 37% by weight=22.0 ml;
remainder: demineralized $H_2O$ up to a volume of 700 ml.

The impregnated powder was dried at 130° C. for 16 hours in an oven previously brought to the intended temperature. This was followed by a second impregnation with the remaining volume of solution, equal to 300 ml, and by final drying at 130° C. for 16 hours in an oven previously brought to the intended temperature.

The chemical and physical characteristics of the catalyst are given in Table 1.

Example 3

1000 g of C gamma $Al_2O_3$ were impregnated a first time in a 5-liter rotating jar at ambient temperature with 400 ml of an aqueous solution having a total volume of 700 ml and containing:

$CuCl_2.2H_2O$=299.6 g;
$MgCl_2.6H_2O$=71.2 g;
KCl=16.2 g;
HCl 37% by weight=22.0 ml;
remainder: demineralized $H_2O$ up to a volume of 700 ml.

The impregnated powder was dried at 130° C. for 16 hours in an oven previously brought to the intended temperature. This was followed by a second impregnation with the remaining volume of solution, equal to 300 ml, and by final drying at 130° C. for 16 hours in an oven previously brought to the intended temperature.

The chemical and physical characteristics of the catalyst are given in Table 1.

Example 4

1600 g of D gamma $Al_2O_3$ were impregnated a first time in a 5-liter rotating jar at ambient temperature with 640 ml of an aqueous solution having a total volume of 1120 ml and containing:
$CuCl_2.2H_2O$=476.0 g;
$MgCl_2.6H_2O$=250.0 g;
HCl 37% by weight=35.0 ml;
remainder: demineralized $H_2O$ up to a volume of 1120 ml.

The impregnated powder was dried at 130° C. for 16 hours in an oven previously brought to the intended temperature. This was followed by a second impregnation with the remaining volume of solution, equal to 480 ml, and by final drying at 130° C. for 16 hours in an oven previously brought to the intended temperature.

The chemical and physical characteristics of the catalyst are given in Table 1.

Example 5

1000 g of E gamma $Al_2O_3$ were impregnated a first time in a 5-liter rotating jar at ambient temperature with 400 ml of an aqueous solution having a total volume of 700 ml and containing:
$CuCl_2.2H_2O$=298.3 g;
$MgCl_2.6H_2O$=116.2 g;
HCl 37% by weight=22.0 ml;
remainder: demineralized $H_2O$ up to a volume of 700 ml.

The impregnated powder was dried at 130° C. for 16 hours in an oven previously brought to the intended temperature. This was followed by a second impregnation with the remaining volume of solution, equal to 300 ml, and by final drying at 130° C. for 16 hours in an oven previously brought to the intended temperature.

The chemical and physical characteristics of the catalyst are given in Table 1.

Example 6

1600 g of A gamma $Al_2O_3$ were impregnated a first time in a 5-liter rotating jar at ambient temperature with 650 ml of an aqueous solution having a total volume of 1100 ml and containing:
$CuCl_2$ $2H_2O$=481.5 g;
$MgCl_2$ $6H_2O$=187.7 g;
HCl 37% by weight=190.0 ml;
remainder: demineralized $H_2O$ up to a volume of 1100 ml.

The impregnated powder was dried at 100° C. for 16 hours in an oven previously brought to the intended temperature. This was followed by a second impregnation with the remaining volume of solution, equal to 450 ml, and by final drying at 100° C. for 16 hours in an oven previously brought to the intended temperature.

The chemical and physical characteristics of the catalyst are given in Table 1.

Comparison Example 1

The catalyst of this example is a commercially available catalyst, supported on gamma alumina which contains 10.06% copper by weight, 0.78% potassium by weight, and 12.15% chlorine by weight, and wherein the X/Y ratio is 0.8, the surface area is 117 $m^2/g$, the pore volume is 0.27 $cm^3/g$; average pore radius is 4.6 nm; 44.9% of the particles have a size between 63 and 125 microns, 39.5% between 40 and 63 microns, and 14.4% below 40 microns. The chemical and physical characteristics of the catalyst are given in Table 2.

Comparison Example 2

The catalyst of this example also is a commercially available catalyst, supported on gamma alumina which contains 12.50% copper by weight and 5.58% chlorine by weight and wherein the X/Y ratio is 3.0, the surface area is 237 $m^2/g$ and the pore volume is 0.34 $cm^3/g$; average pore radius is 2.9 nm; 60.6% of the particles have a size between 63 and 125 microns, 20.5% between 40 and 63 microns, 15.9% below 40 microns. The chemical and physical characteristics of the catalyst are given in Table 2.

Example 7

The catalyst of Example 4 was tested in the test conditions of said Example 4, with the only difference that the operating pressure was 2 atm instead of 1.6 atm, with a linear velocity of 10 cm/s instead of 21 cm/s, and with a Cl/C ratio of 0.56 instead of 0.61, and an $O_2/C_2H_1$ ratio of 0.31 instead of 0.43.

The results obtained in a test conducted at 220° C., compared with the results obtained with the catalyst of Comparison Example 1 used in the same condition, are listed below.

|  |  | Molar $C_2H_4$ selectivity % to | | Molar DCE |
|---|---|---|---|---|
| EXAMPLE | HCl conv. | DCE | COx | purity % |
| 1 | 99.68 | 98.88 | 0.57 | 99.45 |
| CMP 1 | 99.66 | 97.86 | 1.43 | 99.28 |

TABLE 1 characteristics of the catalyst according to the invention

| | EXAMPLES | | | | | |
|---|---|---|---|---|---|---|
| | 1 | 2 | 3 | 4 | 5 | 6 |
| | ALUMINA TYPE | | | | | |
| | B | C | C | D | E | A |
| CHEMICAL COMPOSITION | | | | | | |

TABLE 1-continued characteristics of the catalyst according to the invention

| | | EXAMPLES | | | | | |
|---|---|---|---|---|---|---|---|
| | | 1 | 2 | 3 | 4 | 5 | 6 |
| | | ALUMINA TYPE | | | | | |
| | | B | C | C | D | E | A |
| Cu | % by weight | 7.92 | 8.14 | 8.23 | 7.77 | 8.11 | 7.92 |
| Mg | " | 1.00 | 1.02 | 0.63 | 1.29 | 1.01 | 0.97 |
| K | " | | | 0.63 | | | |
| | SURFACE COMPOSITION (XPS) | | | | | | |
| Al/Cu (Y) | atomic ratio | 12.5 | 12.1 | 12.0 | 12.6 | 12.1 | 13.8 |
| Al/Cu (X) | " | 27.0 | 30.0 | 34.5 | 33.4 | 19.2 | 25.5 |
| X/Y | " | 2.2 | 2.5 | 2.9 | 2.6 | 1.6 | 1.8 |
| | PHYSICAL CHARACTERISTICS | | | | | | |
| Surface area | $m^2/g$ | 130 | 124 | 119 | 116 | 128 | 119 |
| Pore volume | ml/g | 0.24 | 0.27 | 0.27 | 0.24 | 0.28 | 0.22 |
| Average radius | nm | 3.9 | 4.4 | 4.5 | 4.1 | 4.4 | 3.7 |
| | PARTICLE SIZE DISTRIBUTION | | | | | | |
| >125 | micron | 0.6 | 2.1 | 2.1 | 1.0 | 2.3 | 2.2 |
| 125-90 | " | 6.4 | 12.2 | 11.6 | 6.2 | 13.5 | 30.3 |
| 90-63 | " | 31.3 | 31.4 | 31.8 | 30.7 | 37.9 | 47.6 |
| 63-40 | " | 43.0 | 40.3 | 42.6 | 43.4 | 39.8 | 18.0 |
| <40 | " | 18.7 | 14.0 | 11.9 | 18.7 | 6.5 | 1.9 |

TABLE 2

Characteristics of catalysts of comparison examples

| EXAMPLES | | CMP1 | CMP2 |
|---|---|---|---|
| | CHEMICAL COMPOSITION | | |
| Cu | % by weight | 10.06 | 12.50 |
| K | " | 0.78 | — |
| | SURFACE COMPOSITION (XPS) | | |
| Al/Cu (Y) | Atomic ratio | 9.6 | 7.3 |
| Al/Cu (X) | " | 7.3 | 21.7 |
| X/Y | " | 0.8 | 3.0 |
| | PHYSICAL CHARACTERISTICS | | |
| Surface area | $m^2/g$ | 117 | 237 |
| Pore volume | ml/g | 0.27 | 0.34 |
| Average radius | nm | 4.6 | 2.9 |
| | PARTICLE SIZE DISTRIBUTION | | |
| >125 | micron | 1.2 | 3.0 |
| 125–90 | " | 9.5 | 22.2 |
| 90–63 | " | 35.4 | 38.4 |
| 63–40 | " | 39.5 | 20.5 |
| <40 | " | 14.4 | 15.9 |

TABLE 3 results of the activity of catalysts in test conditions OXY 1

| EXAMPLE | HCl conv. % | Molar $C_2H_4$ selectivity % to DCE | COx | Molar DCE purity % |
|---|---|---|---|---|
| | AVERAGE TEMPERATURE 210° C. | | | |
| 1 | 99.95 | 96.96 | 2.63 | 99.58 |
| 2 | 99.94 | 97.22 | 2.45 | 99.66 |
| 3 | 99.88 | 97.15 | 2.31 | 99.45 |
| 4 | 99.93 | 97.80 | 1.80 | 99.60 |
| 5 | 99.91 | 97.61 | 1.99 | 99.60 |
| CMP 1 | 99.92 | 96.56 | 2.93 | 99.48 |
| CMP 2 | 99.93 | 94.61 | 5.00 | 99.60 |
| | AVERAGE TEMPERATURE 220° C. | | | |
| 1 | 99.96 | 95.83 | 3.81 | 99.63 |
| 2 | 99.93 | 96.31 | 3.24 | 99.54 |
| 3 | 99.92 | 96.35 | 2.97 | 99.30 |
| 4 | 99.98 | 96.84 | 2.71 | 99.54 |
| 5 | 99.93 | 96.69 | 2.85 | 99.54 |
| 6 | 99.96 | 96.90 | 2.69 | 99.57 |
| CMP 1 | 99.96 | 95.29 | 4.02 | 99.28 |
| CMP 2 | 99.91 | 93.96 | 5.51 | 99.43 |
| | AVERAGE TEMPERATURE 230° C. | | | |
| 1 | 99.96 | 94.92 | 4.61 | 99.50 |
| 2 | 99.93 | 96.12 | 2.46 | 99.57 |
| 3 | 99.96 | 94.73 | 4.45 | 99.15 |
| 4 | 99.95 | 95.67 | 3.91 | 99.57 |
| 6 | 99.99 | 96.69 | 2.85 | 99.54 |
| CMP 1 | 99.93 | 94.62 | 4.54 | 99.12 |
| CMP 2 | 99.65 | 93.47 | 6.00 | 99.44 |

TABLE 4

Results of activity of catalysts in test conditions OXY 2.

| EXAMPLE | HCl conv. % | Molar $C_2H_4$ selectivity % to DCE | COx | Molar DCE purity % |
|---|---|---|---|---|
| | AVERAGE TEMPERATURE 210° C. | | | |
| 2 | 99.88 | 99.21 | 0.51 | 99.72 |
| 3 | 99.82 | 99.24 | 0.40 | 99.64 |
| CMP 1 | Test not completed due to defluidization | | | |

TABLE 4-continued

Results of activity of catalysts in test conditions OXY 2.

| EXAMPLE | HCl conv. % | Molar C$_2$H$_4$ selectivity % to | | Molar DCE purity % |
|---|---|---|---|---|
| | | DCE | COx | |
| | | of catalytic bed due to sticking | | |
| AVERAGE TEMPERATURE 220° C. | | | | |
| 2 | 99.93 | 98.03 | 1.66 | 99.69 |
| 3 | 99.74 | 97.51 | 2.16 | 99.66 |
| 4 | 99.92 | 98.55 | 1.10 | 99.65 |
| CMP 1 | 99.92 | 96.99 | 2.49 | 99.47 |
| AVERAGE TEMPERATURE 230° C. | | | | |
| 3 | 99.91 | 96.61 | 2.85 | 99.45 |
| 4 | 99.88 | 98.09 | 1.56 | 99.64 |
| CMP 1 | 99.90 | 96.34 | 3.06 | 99.39 |

The disclosures in Italian Patent Application No. MI2004A002317 from which this application claims priority are incorporated herein by reference.

What is claimed is:

1. A process for preparing catalysts for oxychlorination of ethylene to 1,2-dichloroethane, comprising compounds of copper and magnesium supported on gamma alumina, wherein the copper, expressed as metal, is present in quantity from 7 to 12% by weight and the Mg/Cu ratio is from 0.05 to 1, wherein the distribution of copper in the catalyst particle is such that the ratio X/Y between the concentration of the copper atoms on the surface given by the Al/Cu ratio (X) and the concentration given by the Al/Cu ratio (Y) in the entire particle is greater than 1.3 and can reach 3, comprising the steps of drying and impregnating the alumina at least twice, wherein the first impregnation stage comprises using volumes of aqueous solution of the Cu and Mg compounds that are equal to, or smaller than, the volume of the pores of the alumina and the second impregnation stage comprises using volumes that decrease with respect to the volume used in the first impregnating.

2. The process according to claim 1, wherein the copper compound of the catalysts is cupric chloride and the magnesium compound is magnesium chloride.

3. The process according to claim 1, wherein the catalysts have a surface area of 60 to 150 mg$^2$/g.

4. The process according to claim 1, wherein the catalysts comprise alkali metal compounds as promoters.

5. The process according to claim 1, wherein the catalysts comprise-alkali metal compounds together with magnesium compounds as promoters.

6. The process according to claim 1, wherein the catalysts are supported on gamma alumina having a surface area between 180 and 250 M$^2$/g and a particle size distribution in which at least 60-80% of the particles have a diameter between 40 and 90 microns.

7. A process of oxychlorination of ethylene to 1,2-dichlorethane, comprising carrying out the oxychlorination in fluid bed formed of a catalyst obtained according to the process of any one of claims 1 to 6, at temperatures from 190° to 240° C., using oxygen as oxidizer and Cl/C molar ratio of 0.5-0.7 and O$_2$/C$_2$H$_4$ ratio of 0.3-0.5.

* * * * *